United States Patent [19]
Teotino et al.

[11] 3,954,778
[45] May 4, 1976

[54] AMINOACETYL DERIVATIVES OF 2,3-DIPHENYL CYCLOPROPYL AMINE

[75] Inventors: Uberto Teotino; Davide Della Bella, both of Milan; Dario Chiarino, Monza, all of Italy

[73] Assignee: Zambon S.p.A., Milan, Italy

[22] Filed: Feb. 26, 1971

[21] Appl. No.: 119,346

[30] Foreign Application Priority Data
  Mar. 3, 1970   Italy .................................. 21404/70

[52] U.S. Cl................ 260/293.76; 260/326.43; 260/562 N; 260/562 B; 424/267; 424/274; 424/324
[51] Int. Cl.² .................................... C07D 295/14
[58] Field of Search........ 260/293.76, 326.3, 562 N, 260/562 B

[56]     References Cited
           UNITED STATES PATENTS
3,192,229   6/1965   Biel .............................. 260/326.3
3,562,276   2/1971   Teotino et al. ..................... 260/268

*Primary Examiner*—G. Thomas Todd
*Attorney, Agent, or Firm*—Stevens, Davis, Miller & Mosher

[57]        ABSTRACT

New aminoacetyl derivatives of 2,3-diphenylcyclopropylamine of the formula

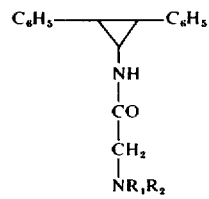

wherein $R_1$ is hydrogen or lower alkyl; $R_2$ is hydrogen, lower alkyl or together with $R_1$ and the nitrogen atom to which they are linked represents a heterocyclic ring, as well as their non toxic addition salts with organic and inorganic acids.

The new compounds are endowed with anticonvulsant and anti-cardiac arrhythmias activity.

3 Claims, No Drawings

AMINOACETYL DERIVATIVES OF 2,3-DIPHENYL CYCLOPROPYL AMINE

The present invention is concerned with new amino acetyl derivatives of 2,3-diphenyl-cyclopropylamine, with the process for the preparation thereof and with pharmaceutical compositions containing them as an active ingredient.

More precisely the invention is concerned with compounds of the formula

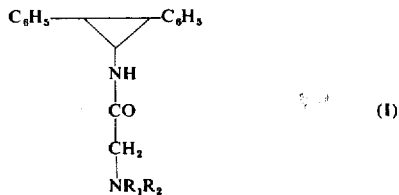

wherein $R_1$ is hydrogen or lower alkyl; $R_2$ is hydrogen, lower alkyl or together with $R_1$ and the nitrogen atom to which they are linked, represents a heterocyclic ring.
as well as with their non toxic addition salts with organic and inorganic acids.

The present invention is also concerned with compounds of the formula

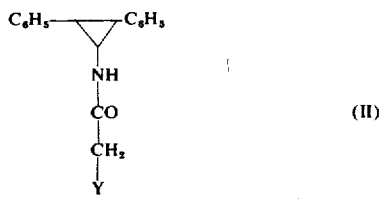

wherein Y is a halogen atom, which are the intermediate products for the preparation of compounds of formula (I).

The new compounds of the invention may exist under the form of geometrical cis-cis, cis-trans and trans-trans isomers besides the form of $d$, $l$ and $dl$ optical isomers.

When it is not explicitly expressed in the course of the present specification, it is intended that we refer both to the single geometrical or optical isomers and to mixtures thereof.

Moreover the present invention protects each and all the above specifically listed isomers.

The process according to which the new compounds of the invention are prepared may be represented by the following scheme:

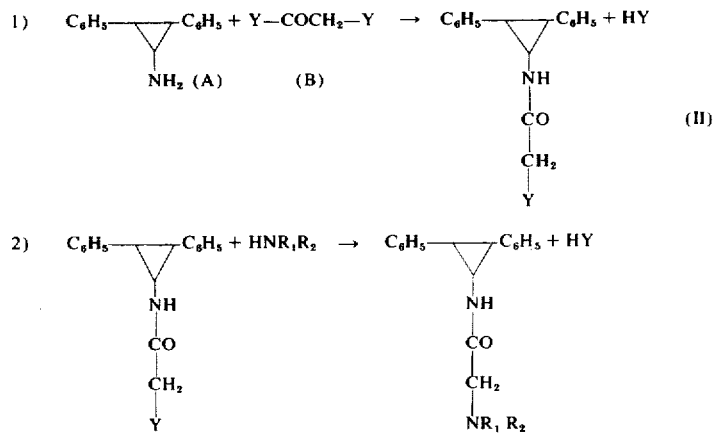

wherein Y, $R_1$ and $R_2$ have the above indicated meaning.

The step (1) is carried out by allowing the compound (A), or an acid addition salt thereof, to react with compound (B), in the presence of an acid binding substance and of an inert solvent or mixture of solvents, at a temperature preferably comprised between 0° and 50°C.

The method preferably used is that according to Schotten-Baumann. The step (2) is carried out by reacting the intermediate compound of formula (II) with an amine of formula $NHR_1R_2$, whrein $R_1$ and $R_2$ have the above indicated meaning, in the presence of an inert solvent or mixture of inert solvents and of an acid binding substance, at a temperature comprised between 50° and 200°C.

It is preferred to use an excess of the amine itself both as acid binding substance and as solvent.

When the amine is a low boiling point one, the reaction is carried out in a sealed tube, while when the amine has a high-boiling point then it is preferred to operate at the boiling temperature of the reaction mixture.

The new compounds according to the invention are highly useful in the therapeutic field due to the significant anticonvulsant and anticardiac arrhythmias activity. The anticonvulsant activity has been measured through the tests of crises (fits) produced with electroshock or with cardiazol.

Materials and methods. The animals used to perform the pharmacological tests with the compounds of the invention have been, unless the contrary is explicitly indicated, male albine Swiss mice weighing 19–23 g; each animal has been used only once.

The compounds have been administered as hydrochlorides, under skin (0.1 ml/10 g) 30 minutes ante; for determining the $LD_{50}$, the compounds have been administered by intraperitoneal route and were considered deaths occured in the 72 hours following the treatment.

As reference compounds there was used: ethosuximide injected under skin 30 minutes ante (before); Phenurone per os 60 minutes ante; phenobarbital sodium salt under skin 30 minutes ante, trimethadione under skin 30 minutes ante; primidone per os 6 hours ante and Mephenesin under skin 30 minutes ante.

Electroshock (M.E.S.) — The method adopted in making the electroshock is Cashin C. H. and Jackson's (J. Pharm. Pharmacol. 1962, 14 (supl. 445) modified as hereinafter described: the electrodes are placed in the outer ear which is filled with physiologic solution before the shock. The applied voltage is of 92 volts with a current (50 Hz) stabilized with a Selonix H.T. 4420 stabilizer; shock duration 0.2 seconds. The animals are considered protected when the extensor phase of the hind paws does not appear during the tonic crisis.

Under such conditions the results obtained with the reference compounds are in good agreement with those reported in the art for the same compounds (E. A. Swinyard, W. C. Brown, L. S. Goodman —J. Pharmacol., 1952, 106, 3 19). Shock by cardiazol (M.M.S.) — 38 mg/kg of cardiazol, in the form of a 0.38% aqueous solution, is quickly injected in the dorsal vein of the mouse's tail (L. S. Goodman, M. Singh Grewal, W. C. Brown, E. A. Swinyard — J. Pharmacol. 1953, 108, 168). The animals are considered as protected when the extensor phase of the hind paws is eliminated during the tonic crisis.

The so-obtained data have been elaborated by calculating the $ED_{50}$ and the $LD_{50}$ according to Lichtfield-Wilcoxon's method (J. Pharmacol. 1949, 96, 99).

The $Ed_{50}$ and $LD_{50}$ values of the reference compounds have been reported in Table 1, while those of the new compounds according to the present invention are reported in Table 2.

TABLE 1

| Reference compounds | M.E.S. $ED_{50}$ mg/kg | M.M.S. $ED_{50}$ mg/kg | $LD_{50}$ mg/kg |
|---|---|---|---|
| Phenurone (1.1-dimethyl-3-phenyl-urea) | 115 (92–132) | 50 (33–75) | |
| Phenobarbital sodium salt | 35 (27.5–46) | 4.5 (2.9–6.9) | 182 |
| Phenitoine Sodium salt | 15 (12.9–17.7) | 7.1 (5.6–8.8) | 120 |
| Trimethadione | | 175 (148.3–206.5) | |
| Primidone | | 5.2 (3.4–7.8) | |
| Ethosuximide | | 50 (36.4–68.5) | |
| Mephenesin | 245 (196–307) | 180 (165.1–196.2) | |

TABLE 2

| Configuration | Formula $R_1$ | Formula $R_2$ | $ED_{50}$ mg/kg M.E.S. | $ED_{50}$ mg/kg M.M.S. | $LD_{50}$ mg/kg |
|---|---|---|---|---|---|
| cis-trans | H | $CH_3$ | 25.5 (22.1–29.3) | 30.0 (25.4–35.4) | 112.0* (93.3–134.0) |
| cis-trans | H | $C_2H_5$ | 16.5 (14.2–19.1) | 13.0 (10.3–16.5) | 85.0* (83.8–86.2) |
| cis-trans | $CH_3$ | $CH_3$ | 16.5 (14.2–19.1) | 16.0 (14.5–17.6) | |
| cis-trans | $C_2H_5$ | $C_2H_5$ | 14.2 (12.5–16.2) | 12.5 (11.1–14.0) | 92.5 (86.5–99.0) |
| cis-trans | n-$C_3H_7$ | n-$C_3H_7$ | >100 mg/kg | 175 (152–201) | |
| cis-trans | iso-$C_3H_7$ | iso-$C_3H_7$ | 135 (121–151) | 87 (62.1–121.8) | |
| cis-trans | n-$C_4H_9$ | n-$C_4H_9$ | >250 mg/kg | >250 mg/kg | |
| cis-trans | ⬠ | | 9 (6.9–11.6) | 5.6 (4.1–7.5) | 67.5 (62.5–72.9) |
| cis-trans | ⬡ | | 14.5 (13.2–15.9) | 6 (4.6–7.8) | 88 (83–93) |
| trans-trans | ⬠ | | 87.0 (75.5–100) | | 266 (238.7–295.3) |

*The compound has been administered as a 2% suspension in gum arabic

As it is evident from the reported data, it has been surprisingly found that the anticonvulsant activity is very good, and even very often higher than that of the best among the known compounds, for these new compounds according to the invention wherein the alkyl radicals bound to the terminal amino groups have 1,2 carbon atoms or form an heterocyclic ring.

Moreover the anticonvulsant activity is higher for the cis-trans compounds than for the trans-trans ones.

The new compounds of the invention are deprived of MAO-inhibiting activity in live rats, both on the mithocondres of hepatic tissue and on the mithocondres of homogenatous of cerebral tissue, even if administered in doses of 100–200 mg/kg per os. As found also with other anticonvulsive drugs, the new compounds of the present invention are endowed with a good antiarrhythmic activity. In particular the activity in cardiac arrhythmias of N-pyrrolidinoacetyl-2,3-cis, trans-diphenylcyclopropylamine has been studied by experimentally inducing arrhythmias in rats by means of calcium chloride, and in dogs by means of adrenaline.

The experiments in rats have been performed as follows:

80 mg/kg of calcium chloride injected by intravenous route in a rat under anesthesia by urethane, cause a reversible arrhythmia which appears within 10 seconds from administration of calcium chloride and disappears in about 5 minutes (Malinow M. e coll. Am.J. Physiol.1953, 172, 743–746). There was determined the inhibiting effect of N-pyrrolidine acetyl-2,3-cis,trans-diphenylcyclopropylamine hydrochloride on the cardiac arrhythmias arising within the 5 minutes following the calcium chloride administration in comparison with quinidine, procaine and propranolol.

The drug is considered active when completely inhibits cardiac arrhythmias.

The N-pyrrolidinoacetyl-2,3-cis,trans-diphenylcyclopropylamine hydrochloride is active at the dose of 2 mg/kg (administration 90 seconds before calcium chloride administration) and the activity lasts about 20 minutes. The active doses of reference drugs under identical conditions are:

quinidine 2.5 mg/kg; procaine 5 mg/kg; propranolol 1 mg/Kg.

The experiments with dogs have been performed as follows:

The dog has been anesthetized with chloralose and then administered by intravenous injection with 30 γ/kg of adrenaline. The results were evaluated according to Somani and Lum B. K. B. (J. Pharmacol. Expt. Therap. 1965, 147, 194–202).

The dog was completely protected by intravenously injecting in the animal 1 mg/kg of N-pyrrolidinoacetyl -2,3-cis,trans-diphenylcyclopropylamine hydrochloride, 2 minutes ante adrenaline administration. The effect lasts 60 minutes.

The pharmacological results have been confirmed in clinical tests. The new compounds of the present invention may be administered either by os or parentherally under pharmaceutically suitable administration form.

Two pharmaceutical compositions which may be prepared are those indicated hereinafter only by way of illustrative examples:

Capsules
N-pyrrolidinoacetyl-2,3-cis,trans-diphenyl
cyclopropyl amine hydrochloride                mg   100
lactose                                         mg   145
talc                                            mg   2.5
magnesium stearate                              mg   2.5
Vials
N-pyrrolidinoacetyl-2.3-cis,trans-diphenyl
cyclopropyl amine hydrochloride                mg   50
distilled water q.s.ad                         ml   2

The hereinafter reported examples have the purpose of illustrating the process for the preparation of the new compounds of the invention, without however limiting the same.

EXAMPLE 1

N-chloroacetyl-2,3-cis,trans-diphenylcyclopropylamine 40.50 g (165 mM) of 2,3-cis,trans-diphenylcyclopropylamine, prepared according to the method described by Kaiser, Burger and Coll. (J. Med. Pharm. Chem. 5(VI), 1243–1265 (1962), are dissolved into 375 ml of water. 950 ml of benzene are added and the solution is cooled to a temperature equal to or lower than 10°C.

A solution of 22.5 g (200mM) of chloroacetyl chloride in 150 ml of benzene and a solution of 17.00 g (415 mM) of NaOH in 300 ml of water are poured drop by drop, at the same time, in the first prepared mixture kept under good stirring.

The addition is completed within 1 hour and half while maintaining the temperature at or lower than 10°C.

After this time the cooling bath is removed and the mixture is kept under stirring for one further hour.

The benzene layer is separated, washed with water and then, successively, with 10% hydrochloric acid, with a 10% aqueous solution of sodium bicarbonate and finally with water.

The benzene extract is dried on anhydrous sodium sulphate and then evaporated.

The residue is pulped with petrol ether and collected on porous septum by filtration under vacuum.

After drying under vacuum at 50°C, 41.5 g of product are obtained. The product may be further purified by crystallisation from isopropyl ether. M.P. 103°–105°C.

In a similar manner the isomer N-chloroacetyl-2,3-trans,trans-diphenylcyclopropylamine is prepared. M.P. 138°–140°C after crystallisation from isopropyl ether.

EXAMPLE 2

N-methylaminoacetyl-2,3-cis,trans-diphenyl-cylcopropylamine hydrochloride

A mixture consisting of 10 g (35 mM) of N-chloroacetyl-2,3-cis,trans-diphenylcyclopropylamine and 50 ml of a 40% solution of methylamine in ethanol (about 650 mM) is placed in a sealed tube and warmed over 12 hours at 80°C.

The reaction mixture is then cooled and dried.

The residue, taken up with water and ethyl ether is shaken at length. The ether phase is separated, washed again with water and dried on anhydrous magnesium sulphate.

The ether solution is filtered and the filtratate added with an ether solution of hydrochloric acid up to acid reaction at Congo Red.

The so obtained precipitate is filtered under vacuum through a porous septum, taken up with boiling ethyl alcohol (180ml) and filtered again. The obtained crystalline product, after drying at 50°C under vacuum, weighs 8.20 g.

The product may be further purified by crystallisation from isopropyl alcohol. M.P. 196°–198°C.

In a similar manner also the N-ethylaminoacetyl-2,3-cis,trans-diphenylcyclopropylamine hydrochloride. M.P. 230°–232°C (crystallized from ethanol) is prepared.

EXAMPLE 3

N-dimethylaminoacetyl-2,3-cis,trans-diphenylcyclopropylamine

A mixture consisting of 15 g (52 mM) of N-chloroacetyl-2,3-cis,trans-diphenylcyclopropylamine and 100 ml of a 30% solution in ethanol of dimethylamine (650 mM) is placed in a sealed tube and warmed at 120°C for 6 hours.

The reaction mixture is then cooled and evaporated to completely eliminate the unreacted ethanol and dimethylamine.

The residue is shaken at the same time with water and ethyl ether. The ether layer is separated, washed with water, dried on anhydrous magnesium sulphate and then evaporated to dryness: yield 13.5 g. The product is crystallized first from hexane and then from isopropyl ether. M.P. 82°–84°C.

In a similar manner also the N-dietylaminoacetyl-2,3-cis-trans-diphenylcyclopropylamine (M.P. 56°–58°C from hexane) and the N-diisopropylaminoacetyl-2,3-cis,trans-diphenylcyclopropylamine (M.P. 101°–103°C from isopropyl ether) are prepared.

EXAMPLE 4

N-di-n-butylaminoacetyl-2,3-cis,trans-diphenylcyclopropylamine

A mixture consisting of 15 g (52mM) of N-chloroacetyl-2,3-cis,trans-diphenylcyclopropylamine and 50 ml (296 mM) of di-n-butylamine is refluxed over 24 hours.

The reaction mixture is cooled and taken up with chloroform. It is then acidified with concentrated hydrochloric acid at Congo Red while maintaining the mixture under stirring and cooling.

The chloroform layer is separated, washed with a saturated aqueous solution of potassium carbonate and then again with water. The chloroform is eliminated after evaporation under vacuum after drying on anhydrous magnesium sulphate.

The so obtained oleous residue is distilled and the fraction distilling at 180°–182°C 0.5 mm Hg collected.

This fraction after standing crystallizes giving 12 g of product at melting point 37°–39°C.

In a similar manner the di-n-propylaminoacetyl-2,3-cis, trans-diphenylcyclopropylamine hydrochloride (M.P. 82°–84°C from ethylacetate is prepared.

EXAMPLE 5

N-pyrrolidinoacetyl-2,3-cis,trans-diphenylcyclopropylamine

A mixture consisting of 120 g (420 mM) of N-chloroacetyl-2,3-cis,trans-diphenylcyclopropylamine and 200 g (2810 mM) of pyrrolidine is refluxed over 15 hours.

The unreacted pyrrolidine is removed by distillation and the residue is taken up with 500 ml of water. Then it is acidified with hydrochloric acid at Congo Red and treated with coal. After filtration the filtrate is alkalized while cooling with a 30% solution of NaOH.

The obtained solution is shaken with ethyl ether, the ether phase separated and washed thoroughly with water, dried on ahydrous magnesium sulphate and ether eliminated by evaporation.

145 ml of semi-solid residue are obtained which is crystallized from 700 ml of isopropyl ether. Yield 115 g of N-pyrrolidinoacetyl-2,3-cis,trans-diphenylcyclopropylamine. M.P. 93°–94°C.

In order to obtain the corresponding hydrochloride, the amine is dissolved in 500 ml of warm absolute ethyl alcohol and added with concentrate hydrochloric acid solution in ethyl alcohol up to acid reaction at Congo Red. Then it is cooled and filtered under vacuum. Yield 116 g.

The product is purified by crystallization from absolute ethyl alcohol. Yield 100 g. M.P. 183°–185°C.

With the same method the following products are prepared: -N-piperidinoacetyl-2,3-cis,trans-diphenylcyclopropylamine hydrochloride; M.P. 100°–102°C (from isopropylether), -N-pyrrolidinoacetyl-2,3-trans,-trans-diphenylcyclopropylamine hydrochloride; M.P. 223°–225°C (from acetonitrile).

All the above reported melting points are not corrected.

We claim:

1. A compound of formula

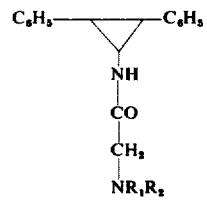

wherein $R_1$ is H or lower alkyl $R_2$ is H, lower alkyl or together with $R_1$ and the nitrogen atom to which they are bound, is pyrrolidino or piperidino. and their non toxic acid addition salts with pharmaceutically suitable organic or inorganic acid.

2. A compound according to claim 1, showing a cis-trans configuration.

3. A compound of formula

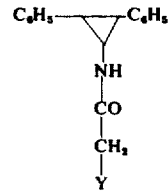

wherein Y is a halogen atom

* * * * *